United States Patent [19]
Allen et al.

[11] Patent Number: 5,264,180
[45] Date of Patent: * Nov. 23, 1993

[54] MOBILE REAGENTS IN AN ANALYTE ASSAY IN A SELF-CONTAINED APPARATUS

[75] Inventors: Michael P. Allen, Sunnyvale; Henry J. Jeong, Palo Alto, both of Calif.

[73] Assignee: ChemTrak, Inc., Sunnyvale, Calif.

[*] Notice: The portion of the term of this patent subsequent to Sep. 25, 2007 has been disclaimed.

[21] Appl. No.: 833,774

[22] Filed: Mar. 9, 1992

Related U.S. Application Data

[63] Continuation-in-part of Ser. No. 474,991, Feb. 6, 1990, Pat. No. 5,132,086, which is a continuation-in-part of Ser. No. 357,045, May 24, 1989, abandoned, which is a continuation-in-part of Ser. No. 324,407, Mar. 16, 1989, Pat. No. 4,987,085, which is a continuation-in-part of Ser. No. 195,881, May 19, 1988, Pat. No. 4,999,287, which is a continuation-in-part of Ser. No. 64,883, Jun. 22, 1987, Pat. No. 4,973,549.

[51] Int. Cl.$^5$ ............................................. G01N 21/00
[52] U.S. Cl. ...................................... 422/56; 422/57; 422/58; 435/970; 436/169; 436/170
[58] Field of Search ................... 422/56, 57, 58, 61; 436/169, 170; 435/970, 11, 28

[56] References Cited

U.S. PATENT DOCUMENTS

| | | | |
|---|---|---|---|
| 4,637,978 | 1/1987 | Dappen | 435/28 |
| 4,680,259 | 7/1987 | Cumbo et al. | 435/19 |
| 4,772,561 | 9/1988 | Genshaw | 435/10 |
| 4,826,759 | 5/1989 | Guire et al. | 436/169 |
| 4,940,660 | 7/1990 | Hirai | 435/7.92 |
| 4,959,324 | 9/1990 | Ramel et al. | 436/169 |
| 4,973,549 | 11/1990 | Khanna et al. | 422/56 |
| 4,987,085 | 1/1991 | Allen et al. | 436/169 |
| 4,999,287 | 3/1991 | Allen et al. | 435/28 |
| 5,132,086 | 7/1992 | Allen et al. | 422/56 |

Primary Examiner—James C. Housel
Assistant Examiner—Laura E. Collins
Attorney, Agent, or Firm—Bertram I. Rowland

[57] ABSTRACT

Non-instrumented assays are providing employing a flow-path with a moveable sample receiving pad, which moves from a sample receiving site to a bridging site between a transport element and a measurement region. A reagent transport solution is employed which comprises enzymes capable of reacting with the analyte to produce hydrogen peroxide, where horseradish peroxidase may catalyze a reaction resulting in the formation of a detectable boundary in the measurement region. The distance of the boundary is indicative of the amount of analyte in a sample.

9 Claims, 1 Drawing Sheet

MOBILE REAGENTS IN AN ANALYTE ASSAY IN A SELF-CONTAINED APPARATUS

CROSS-REFERENCE TO RELATED APPLICATIONS

This application is a continuation-in-part of application Ser. No. 474,991, filed Feb. 6, 1990, now U.S. Pat. No. 5,132,086, which is a continuation-in-part of application Ser. No. 357,045, filed May 29, 1989, now abandoned which application is a continuation-in-part of application Ser. No. 324,407, filed Mar. 16, 1989, now U.S. Pat. No. 4,987,085, which is a continuation-in-part of application Ser. No. 195,881, filed May 19, 1988, now U.S. Pat. No. 4,999,287 and a continuation-in-part of application Ser. No. 64,883, filed Jun. 22, 1987, now U.S. Pat. No. 4,973,549, which are incorporated herein by reference.

INTRODUCTION

1. Technical Field

The field of this invention relates to analyte immunoassays.

2. Background

With the increasing availability of drugs for the treatment of a variety of diseases, the identification of a wide variety of compounds associated with particular pathogens, and the need to detect small amounts of contaminants in a wide variety of natural fluids in the environment or in processing plant effluents, there has been a concomitant expansion in methods for measuring analytes. For the most part, the measurement of analytes has occurred in clinical laboratories, where skilled technicians are able to perform a diversity of measurements with sophisticated equipment and reagents. However, there has been an ever greater need to allow for untrained people to perform assays, in doctors' offices, in the home, and in counseling clinics.

For assays to be carried out outside of clinical laboratories, it is desirable that the equipment, if any, required to read the results is simple and inexpensive, that a minimum number of reagents must be mixed and measured, that the sample be either easily measured or there be no requirement for measurement, that the protocol involve as few steps as possible and the assay be relatively insensitive to changes in the environment and actions of the operator. In addition, any device should be sturdy, relatively small, and have few, if any, moving parts. There is, therefore, substantial interest in developing assays which allow for non-technical people to obtain reproducible results without requiring sophisticated equipment to determine the assay value.

3. Relevant Literature

U.S. Pat. No. 4,959,324 describes an apparatus which is self-contained for detecting analytes which serve as enzyme substrates. Other patents of interest include: U.S. Pat. Nos. 4,987,085 and 4,999,287, as well as the references contained in the aforementioned patents.

SUMMARY OF THE INVENTION

Methods are provided for performing assays in a self-contained apparatus, where the assays involve the analyte as an enzyme substrate and the product of the enzymatic reaction is determined by the extent of reaction of such enzyme product with a reactant bound non-diffusibly in an extended measurement region. The method employs an apparatus which has a continuous flow-path having at least three regions, a fluid transport region, a sample region and a measuring region. The sample region is prevented from fluid transfer contact with the other portions of the flow-path prior to receiving the sample. After the sample region receives the sample, it is brought into fluid transfer relationship with the other regions, and the fluid transfer region contacted with fluid comprising at least one assay reagent to permit the reagent solution to pass through the sample region and into the measuring region. The measuring region has bound to it a non-diffusibly bound reactant which provides for a visible boundary, where the distance of the boundary is related to the amount of analyte.

BRIEF DESCRIPTIONS OF THE DRAWINGS

DESCRIPTION OF SPECIFIC EMBODIMENTS

Figure 1:
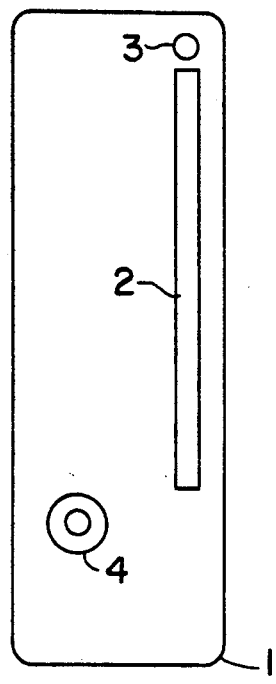
FIG. 1 is a diagrammatic plan view of a plate which covers the base plate.

Methods and apparatus are provided for performing assays in a self-contained apparatus, where the analyte is an enzyme substrate and the enzyme is a member of a reagent system, resulting in color production. The apparatus comprises a flow path which is interrupted prior to receiving the sample, but becomes continuous after receiving the sample, reagents bound to a bibulous support, a source of an eluent for initiating the assay, and means for bringing the sample receiving element from a position in which it is out of liquid transfer relationship with the other members of the flow path to a position where it is in liquid transfer relationship with the other members of the flow path. The flow path is primarily divided into three parts:

(1) a bibulous short element which serves by capillary action to wick transport reagent solution to the sample receiving element; the sample receiving element; and the measuring region, where the downstream portion of the measuring region may serve a plurality of functions, serving to provide a threshold value by removing a predetermined amount of a reagent, allowing for mixing, providing a source of reagent(s) or the like. The flow path will be comprised for the most part of a bibulous material which absorbs a hydrophilic liquid and allows for transport of the reagents contained in the reagent solution, without chromatographing the components of the reagent solution to a significant extent.

The sample receiving element or region will normally serve a plurality of functions. The sample receiving element will receive the sample, serve as a bridge for transport of fluid between adjacent elements of the flow path, serve to measure the volume of the sample, and in certain instances may include one or more reagents which may affect the observed signal. The sample receiving element prior to initiation of the assay will be prevented from acting as a bridging element between adjacent members of the flow path and at or subsequent to initiation of the assay will serve as such bridging element. After receiving the sample, the sample receiving element is acted upon so as to become a bridging element in the flow path, the action normally involving movement of the sample receiving element from a position where it is out of fluid transport relationship to a position where it is in fluid transport relationship with the adjacent members of the flow path.

The measuring element or region including a detection zone will be an extended member, which allows for flow of the reagent solution through the measuring element by means of capillary action. The measuring element will have one or more members of a signal-producing system present on the measuring element, where the height or distance of the signal border e.g. a distance from the sample receiving element to the signal front, will be related to the amount of analyte in the sample and on the sample receiving member. By appropriate choice of members of the signal producing system for a quantitative assay, visually observable fronts may be obtained involving color in the visible region, fluorescent signals, or the like.

In addition, the measuring element may have one or more additional regions between the measuring region and the sample receiving element. These regions may serve to control the dynamic range of the assay, to provide a delay before the elements of a signal producing system move into the measuring region, to allow mixing or a reaction to occur, and the like. By providing for a reaction in this region with a member of the signal producing system, the dynamic range of the assay will be changed in the measuring region. Also, where a plurality of enzymes are involved, there may be one of the enzymes bound in this region to ensure complete reaction of the analyte.

Since for many analytes there may be a threshold value which may be of interest and values below the threshold value are not of interest, one may provide a sufficient amount of reagent in a threshold contact region to react with a member of a signal producing system, so that the threshold value becomes a zero or low value observed in the measuring region. The reaction may be as a result of reaction of the enzyme product with the reagent, for example, reaction of hydrogen peroxide with a reductant. The mixing region will usually be a bibulous member which serves to transport the liquid medium from the sample receiving element to the measuring zone or threshold zone.

Various techniques may be employed for inhibiting fluid flow to and from the sample receiving element to the other element involved in the flow path. Of particular interest is the use of a slide which can be moved from a first position, where the sample receiving element receives the sample, to a second position where the sample receiving element serves as a bridge between the adjacent members of the flow path. The slide prevents sample spreading to the other elements of the flow path, before it is time to carry out the assay.

The path of the sample receiving element moving from the site at which the sample is received to the site where it is in the flow path, may provide means for removing excess sample from the sample receiving element. Such means provide for a quantitative measure of the amount of sample received by the sample receiving element. Thus, by having a region in the path of the slide which is narrowed, so as to remove unabsorbed sample medium, without significantly squeezing the sample receiving element, the amount of sample absorbed by the sample receiving element may be relatively accurately reproduced. The narrowing may be as a result of a convexity, such as a rod in relief, a roller or any other convenient scraping means. The narrowing of the path should provide a space about equal to or slightly less than the wet thickness of the sample receiving element. The slide, therefore, not only serves to move the sample receiving element, but also to meter the amount of fluid absorbed by the sample receiving element.

The slide may also serve an additional function in releasing the reagent containing transport solution. In providing for a self-contained device, the solution may be packaged in a sealed container, e.g. a scorable pouch, where the pouch may be situated in a chamber, where the chamber is situated in the device above a well for receiving the solution. The slide is provided with an arm which has protruding means, e.g. teeth, which can score or rip the seal of the pouch to release the solution. Instead of a pouch, one may provide for a foil which closes the bottom of the chamber, which foil may be scored or ripped to open. It is found that with an undesirable frequency, the solution in the chamber is not released when the seal is scored.

Methods for increasing the efficiency of release include providing a bibulous strip with a tongue extending from the scoring arm to the well region adjacent the transport element which extends into the well, where upon movement of the scoring arm, the strip moves into the chamber and initiates flow. Alternatively, one can provide for a path for the scoring arm, where the scoring arm undergoes a rapid drop after having scored a substantial portion of the length of the seal, where the sudden shock results in solution flow. Thus, with movement of the slide, one may move the sample receiving element, monitor the amount of sample associated with a sample receiving element, and release the transport or reagent solution for development of the assay.

The subject assay finds particular use with analytes which are substrates for enzymes, where a product is produced which can be readily detected by one or more successive reactions. Thus, analytes such as cholesterol or its esters, urea, glucose, and the like may be employed, where each of these substances will react with an oxidase to provide an oxidizing species. The oxidizing species may then react, either directly or indirectly, with the compound non-diffusibly bound in the measurement region, where a detectable boundary will be produced, where its distance from some pre-determined site will be related to the amount of analyte in the sample. Illustrative of this situation would be the hydrolysis of serum cholesterol ester by cholesterol esterase (EC:3.1.1.13) and subsequent oxidation of cholesterol by cholesterol oxidase (EC:1.1.3.6) to produce a stoichiometrically identical amount of hydrogen peroxide. This hydrogen peroxide may then react with MBTH catalyzed by horseradish peroxidase (HRP), with the HRP in the mobile phase or fixed in the measurement region, resulting in a product in association with the non-diffusibly bound reactant to produce a detectable boundary.

Where blood is the sample, the sample receiving element may be positioned under a red blood cell removing filtering device. The blood sample will normally be one or a series of small drops, generally having a total volume under about 100 $\mu$L more usually from about 10 to 50 $\mu$L. The layers through which the sample flows will usually include a mesh layer, a first membrane, and a second membrane cooperating with the first membrane to insure the substantially complete removal of any interfering cells from the blood sample. The first layer of the separation member is used to reduce the concentration of red and white blood cells received by the second filtration member. Since the first membrane acts as a coarse separation means, the first membrane may take any of a wide variety of forms.

Various packings or sieving depth filters may be employed, such as glass fibers, cellulose or glass filters treated with red blood cell capture reagents, glass fiber filters, synthetic fiber filters or a composite material including any combination of the above materials. Glass fiber filters are available from such manufacturers as Whatman, Schleicher & Schuell, MSI, and Pall. The glass fiber filters are further characterized by a glass fiber diameter in the range of about 0.05–9μ and a density of about 50–150 g/m². The glass fiber filters may be illustrated by S & S Glass 30, Whatman GFD, and S & S 3662. The second membrane, when present, will be in fluid receiving relationship with the first membrane, and have an average porosity in the range of about 0.2μ to 7μ, preferably about -5μ, where the pores may or may not be of substantially uniform diameter through the membrane. When an asymmetric membrane is employed, desirably the membrane will have a minimum porosity not less than about 0.4μ, preferably not less than about 0.45μ and a maximum porosity not greater than about 40μ, usually not greater than about 20μ. Illustrative microporous membranes include Filtrite polysulfone asymmetric, 20μ–0.45μ, Sartorious cellulose acetate 1.2μ, Nucleopore 0.4–5 μm polycarbonate, etc.

The sample receiving element will be immediately beneath the red blood cell removing membrane(s) and in fluid receiving relationship with the membrane(s). The sample receiving element will normally be a bibulous member able to absorb a sample fluid and will usually include cellulosic materials, e.g. paper, or the like. A sample receiving element will usually be of a size in the range of about 5 to 50 mm² surface area and a thickness in the range of about 0.1 to 2 mm, having a volume capacity in the range of about 1–30 μL.

The sample may be any convenient sample, which includes physiologic fluids, e.g. blood, plasma, urine, cerebrospinal fluid, ocular lens fluid, etc., waste streams, effluents, soil, water sources, foods, etc.

The reagent solution will have, in addition to any peroxidase present, at least one enzyme acting on the analyte present, normally in sufficient amount so as not to be rate-limiting upon encountering the analyte at the sample receiving element. For cholesterol, enzymes which may be present, include cholesterol esterase, cholesterol oxidase and horseradish peroxidase, where these will also be present in non-rate limiting amounts. Generally, the oxidase will be present in from about 0.1–100 IU/ml, more usually from about 0.5–10 IU/ml, with a similar concentration for the esterase in the case of cholesterol. A similar concentration range will also serve for the peroxidase.

Sufficient substrates and co-factors will be provided, so as not to be rate-limiting. Generally, the concentration of the individual component will not exceed about 1M, usually not exceeding about 0.5M.

Buffers normally present provide a buffered solution having a pH in the range of about 6–10, usually about 6.5–9, generally being at concentrations of about 50–500 mM. Various buffers may be employed, such as Tris, phosphate, carbonate, MOPS, or the like. The particular buffer will be chosen in accordance with the enzyme, so as to minimize any adverse effect of the buffer. Other additives which may be included are salt to provide the desired ionic strength, stabilizers, biocides, and the like.

Various compounds may serve as the non-diffusibly bound reagent, such as tetramethylbenzidine, 1-chloro-4-napthol, 2,2'-azinobis(3-ethylbenzothiazoline-6-sulfonic acid),diammonium salt, dicarboxidine, substituted dialkylanilines, etc. These reagents may be bound to the bibulous support in accordance with conventional ways. See for example U.S. Pat. No. 4,973,549.

The materials used for the flow-path elements may be any bibulous material, usually having a thickness in the range of about 0.05 to 2 mm, more usually 0.15 to 0.75 mm. A wide variety of bibulous supports may be employed, particularly cellulosic supports, such as chromatography paper, silica on a support, alumina on a support, polymeric membranes such as nitrocellulose and nylon, etc. The characteristics of the bibulous material employed for the measurement region may include the need for covalent bonding, irreversible binding of the detectable label, development of a clear and sharp border, and a convenient flow rate.

The entire flow-path may have a length of about 25 to 200 mm, more usually from about 50–150 mm, preferably about 100 mm. About 25% to 90% of the length of the flow path will be the measurement region, comprising a quantitation zone, optionally a mixing zone and/or threshold value zone. The mixing and/or threshold value zone will generally be a total of about from 5% to 35% of the flow-path. The transport element will generally be from about 5–25 mm, being about 10% to 20% of the flow-path. A sample receiving element will generally be from about 1–10% of the flow path. The width of the strips may be varied widely, usually being at least 2 mm and not more than about 10 mm, preferably from about 3–7 mm. The two strips will usually each overlap the sample receiving element by at least about 0.2 mm and not more than about 2 mm, usually about 1 mm, being primarily a matter of convenience.

In order to carry out an analyte measurement, such as cholesterol, the user lances a finger or other source of blood and applies a hanging drop of blood to the application site, which is a white central well with a red border. When the white center is no longer visible, a sufficient amount of blood has been applied. The user then waits about 30 seconds to 2 min. or more to allow adequate filtration and recovery of plasma onto the sample receiving element pad.

The slide is then pulled until it snaps into place. At this point, the sample receiving element pad containing the plasma sample has been metered by a squeegee metering bar and is brought into contact in fluid transferring relationship with the transfer region and the measurement region over about a 2 mm gap. The foil seal of the reagent solution or transport solution containing pouch in the well of the coverplate is sheared, releasing the solution into the receiving well in the baseplate. This begins the wicking of the strip assembly which washes the sample from the receiving pad, reacts with the analyte to form hydrogen peroxide and carries all of the mobile elements through the measurement region.

All of this happens automatically without intervention by the operator. When the reagent solution has reached a predetermined site, sufficient time will have occurred for the hydrogen peroxide to be substantially completely spent and the detectable boundary can then be measured as an indication of the amount of analyte in the sample.

For further understanding of the invention, the drawings will now be considered.

Figure 2:
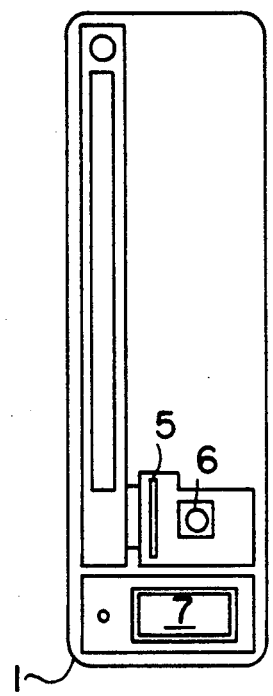
FIG. 2 is a diagrammatic plan view of the underside of the cover plate.
Figure 3:
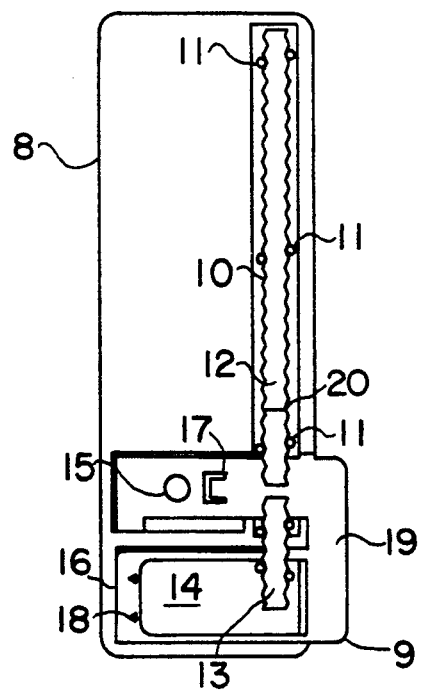
FIG. 3 is a diagrammatic plan view of the base plate and slide of a device according to the subject invention.

In FIG. 1, a top view of cover plate 1 is shown, where viewing window for slot 2 allows one to view the measuring region, while indicator hole 3 indicates when the transport solution has completely traversed the measurement region. An orifice 4 is provided for introduction of the sample. In FIG. 2, a bottom view of cover plate 1 is shown, where squeegee metering bar 5 for removing excess fluid from the sample receiving element is present adjacent orifice 6 which communicates with orifice 4 and holds the filters or membranes for separating the cells from blood samples. A chamber 7 is provided for holding the transport solution. In FIG. 3, a top view of the base plate is provided with slide 9. A slot 10 is present for receiving the measurement strip 12. Slot 10 provides locating pins 11 for orienting the measurement strip, where the edges of the measurement strip are serrated to improve the sharpness of the border. Wicking strip 13 extends into well 14 which receives the transport solution which is contained in chamber 7. Slide 9 has two arms, one arm having opening 15 for receiving the sample receiving element and the other arm 16 which has protruding teeth 18 for scoring a sealing foil enclosing the transport solution in chamber 7. By moving slide handle 19 away from base plate 8, the sample receiving element in hole 15 is moved into a position between strips 12 and 13 to act as a bridge for the transport solution, while scoring teeth 18 open the transport solution container in chamber 7 so that the solution may flow into well 14 and be wicked by transport element 13. A snap 17 for locking the slide in place is provided, so that once the slide is extended it cannot be returned to its initial position.

The measurement region may be impregnated with a peroxidase substrate, particularly a benzothiazoline hydrazone e.g. 3-methyl-2-benzothiazolinone hydrazone (MBTH), or the peroxidase substrate may be in the transport solution. The hydrazone finds particular use with a substituted N,N-dialkyl aniline. The reaction of the bound substrate with oxidized MBTH provides for a colored region with a defined boundary, therefore giving the user a precise reading of the analyte level above a threshold level. This reading is made and the color indicator site above the viewing slide shows the test is complete. Normally, it will take less than about 15 min. for the assay to be complete, reading the peak of a blue area in the viewing slot.

The following examples are offered by way of illustration and not by way of limitation.

EXPERIMENTAL

This example illustrates separation between cholesterol levels that is obtained through placement of the cholesterol conversion reagent on the strip in the transfer region, in the region between the sample receiving and measurement region, on the sample receiving element, or in the transport solution.

In carrying out the assay for cholesterol, a device was prepared having an overall length of about 95 mm; 12 mm of which was the transfer region, about 7 mm was for the sample receiving pad, and the remainder was the measurement region. The strip was made of Whatman 31ET paper, where a modified N,N-dimethylaniline was covalently linked to the paper with MBTH being immobilized passively in the measurement region. This strip configuration was used when the cholesterol conversion reagents are on the sample receiving pad, the transfer region or in the transport solution. When the conversion reagents are positioned between the sample receiving and measurement regions, an additional strip area is included directly upstream from sample receiving area. This strip area is 7 mm long and is called the conversion pad.

The conversion solution comprised 5.33 g sodium phosphate dibasic, 1.25 g sucrose, 1 ml Nonidet P-40, 1.0 g cholic acid, 0.83 g Mega-8, 0.71 g sodium tartrate, 0.65 g sodium nitroprusside, 0.577 g sodium stannate, and 0.01 g sodium azide, after the addition of which the solution was adjusted to pH 7.0, and 1800 units of cholesterol esterase and 5000 units of cholesterol oxidase added thereto, and the volume brought to 100 ml. For the soluble enzymes, the formulation was: 5 Uml of each of cholesterol esterase and cholesterol oxidase, 25 $\mu$g/ml HRP, 2 mg/ml BSA, 0.1M phosphate buffer, pH 7, 0.5% sodium cholate and 0.05% Nonidet-P40. As appropriate, the strip was wetted with this solution in the conversion region and dried. Each test with reagents on the strip contains about 0.18 units cholesterol esterase and 0.60 units of cholesterol oxidase.

The wicking buffer or transport solution was comprised of 0.05M sodium phosphate, 2 mg/ml BGG, 0.005 mg/ml HRP, 0.01% gentamycin, and 0.1% Nonidet P-40.

The resulting device was tested using three calibrators at different levels provided by the College of American Pathologists (CAP), with cholesterol levels at 137, 234 and 333 mg/dl which use lyophilized human serum. Calibrators were reconstituted fresh each day.

Four modifications of the above device were tested for separation (in mm) between the tri-level CAP calibrators. The device modifications involved the location of the conversion reagents: (A) sample receiving region, (B) transport solution; (C) transfer region, and (D) region between the sample receiving and measurement regions.

In carrying out the assay using the above four device configurations, a 10 $\mu$l serum sample was placed on the sample receiving pad, and the transport solution allowed to wick up the strip. The cholesterol reacts with the conversion reagents, specifically the cholesterol esterase and cholesterol oxidase to form hydrogen peroxide, which in turn reacts with the MBTH in the present of the horseradish peroxidase solution to produce a blue color. After the wicking was complete, the color front height was measured, which color front height is directly correlatable with the serum cholesterol level.

TABLE 1

| Location of Conversion Reagents | Cholesterol (mg/dl)[1] | | | Signal Separation (mm) | | |
| --- | --- | --- | --- | --- | --- | --- |
| | 137 | 234 | 333 | 137–234 | 234–333 | 137–333 |
| A. Sample Receiving Region | 27.3 | 34.0 | 41.2 | 6.7 | 7.2 | 13.9 |
| B. Transport Solution | 34.5 | 42.0 | 46.5 | 7.5 | 7.5 | 12.0 |
| C. Transfer Region | 26.0 | 34.7 | 41.3 | 8.7 | 6.6 | 15.3 |
| D. Region Between Sample Receiving and Measurement | 26.0 | 33.7 | 41.3 | 8.7 | 7.6 | 15.3 |

TABLE 1-continued

| | Cholesterol (mg/dl)[1] | | | Signal Separation (mm) | | |
|---|---|---|---|---|---|---|
| Location of Conversion Reagents | 137 | 234 | 333 | 137-234 | 234-333 | 137-333 |
| Regions | | | | | | |

[1]College of American Pathologists serum calibrator set.

It is evident from the above results that a number of substantial advantages accrue by employing the subject methodology, where the reagents are present in a buffered medium and can be stored for long periods of time while substantially maintaining their activity. The enzymes can rapidly react with the analyte in solution and ensure stoichiometric reaction, so as to provide for an accurate result. In addition, high reproducibility is achieved, since variations in reactivity resulting from binding to solid supports may be avoided.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A device for determining the cholesterol level in a sample, said device comprising:
   (1) in the direction of flow of a transport reagent medium, a flow path comprising:
      (a) a transport reagent medium;
      (b) a first bibulous strip comprising a transfer region for transporting said transport reagent medium from a transport reagent medium source;
      (c) a bibulous member comprising a sample receiving region; and
      (d) a second extended bibulous strip comprising a measurement region;
   (2) a signal producing system including:
      (e) cholesterol esterase and cholesterol oxidase, wherein at least one of cholesterol esterase and cholesterol oxidase is present in at least one of said transport reagent medium and said flow path prior to said measurement region;
      (f) peroxidase present in at least one of said transport reagent medium and said flow path including said measurement region;
      (g) a leuco dye member comprising a first dye and a second dye which produces a detectable color, said leuco dye member non-diffusibly bound in said measurement region; and
   (3) means for moving said sample receiving region from a first position out of fluid transferring relationship with said first bibulous strip and said second extended bibulous strip to a second position in fluid transferring relationship.

2. A device according to claim 1, wherein said cholesterol esterase and cholesterol oxidase are in said transport reagent medium.

3. A device according to claim 1, wherein said leuco member is a substituted aniline and said second dye member is a benzothiazolinone hydrazone.

4. A device according to claim 1 further including a cell filtering medium positioned above said bibulous member at said first position.

5. A device for determining the cholesterol level in a sample, said device comprising:
   (1) in the direction of flow of a transport reagent medium, a flow path comprising:
      (a) a transport reagent medium;
      (b) a first bibulous strip comprising a transfer region for transporting said transport reagent medium from a transport reagent medium source;
      (c) a bibulous member comprising a sample receiving region; and
      (d) a second extended bibulous strip comprising a measurement region;
   (2) a signal producing system including:
      (e) cholesterol esterase and cholesterol oxidase, wherein cholesterol oxidase is present in said transport reagent medium, and cholesterol esterase is present in at least one of said transport reagent medium and said flow path prior to said measurement region;
      (f) peroxidase present in at least one of said transport reagent medium and said flow path including said measurement region;
      (3) a dye couple comprising first and second dye members, said first dye member being a N,N-dialkyl aniline which upon coupling with said second dye member activated as a result of a peroxidase catalyzed reaction between hydrogen peroxide and said second dye member produces a detectable color, said N,N-dialkyl aniline non-diffusibly bound in said measurement region; and
   (3) means for moving said sample receiving region from a first position out of fluid transferring relationship with said first bibulous strip and said second extended bibulous strip to a second position in fluid transferring relationship.

6. A method for quantitating cholesterol in a sample employing a signal producing system having a plurality of reagents being distributed between being bound non-diffusibly to a surface or free in solution, said signal producing system with said cholesterol producing a detectable signal in a detection zone on a measuring strip employed as said surface, said signal producing system comprising cholesterol esterase, cholesterol oxidase, peroxidase, and two dye forming members, which upon one of the members in solution undergoing a reaction catalyzed by said peroxidase couples with said other member non-diffusibly bound to said surface, wherein a colored product is formed, said method comprising:

applying sample to a sample receiving element capable of moving from a first position to a second position, said second position in liquid transferring relationship with a measuring strip;

moving said sample receiving element to said second position;

transporting a transport reagent solution comprising at least one of cholesterol esterase and cholesterol oxidase to said sample receiving element for transporting one dye forming member in solution in a detection zone;

allowing said transport reagent solution to wick through said measuring strip with formation of a detectable boundary at a distance from said sample receiving element in relation to an amount of cholesterol in said sample.

7. A method according to claim 6, wherein peroxidase is non-diffusibly bound in said detection zone.

8. A method according to claim 6, wherein said cholesterol esterase is present in relation to at least one of said transport reagent solution, said sample receiving element or between said sample receiving element and said detection zone.

9. A method according to claim 6, wherein said sample is blood, further including filtering said blood prior to applying said sample to said sample receiving element.

* * * * *